US008162840B2

(12) United States Patent
Rosenberg

(10) Patent No.: US 8,162,840 B2
(45) Date of Patent: Apr. 24, 2012

(54) HIGH POWER ULTRASOUND TRANSDUCER

(75) Inventor: Avner Rosenberg, Bet Shearim (IL)

(73) Assignee: Syneron Medical Ltd, Yokneam Illit (IL)

(*) Notice: Subject to any disclaimer, the term of this patent is extended or adjusted under 35 U.S.C. 154(b) by 886 days.

(21) Appl. No.: 12/199,778

(22) Filed: Aug. 27, 2008

(65) Prior Publication Data

US 2010/0016727 A1 Jan. 21, 2010

Related U.S. Application Data

(60) Provisional application No. 61/081,110, filed on Jul. 16, 2008.

(51) Int. Cl.
*A61B 8/14* (2006.01)

(52) U.S. Cl. ........ 600/459

(58) Field of Classification Search ........ 601/2
See application file for complete search history.

(56) References Cited

U.S. PATENT DOCUMENTS

| | | | | |
|---|---|---|---|---|
| 5,353,798 A * | 10/1994 | Sieben | .......... | 600/462 |
| 6,436,051 B1 * | 8/2002 | Morris et al. | .......... | 600/459 |
| 2005/0075573 A1 * | 4/2005 | Park et al. | .......... | 600/459 |
| 2008/0125658 A1 * | 5/2008 | Lee et al. | .......... | 600/459 |

* cited by examiner

*Primary Examiner* — Tse Chen
*Assistant Examiner* — Hien Nguyen
(74) *Attorney, Agent, or Firm* — Smith Risley Tempel Santos LLC; Gregory Scott Smith

(57) ABSTRACT

Disclosed is a high power ultrasound transducer consisting of piezoelectric ceramic elements, an acoustic impedance matching plate, and an assembly of electric contacts arranged to provide voltage to each of said piezoelectric elements. One or more resilient electrically conductive elements enable electric contact between the piezoelectric elements, the impedance matching plate, and the assembly of electric contacts. Disclosed are also an apparatus and method of using the transducer.

35 Claims, 6 Drawing Sheets

HIGH POWER ULTRASOUND TRANSDUCER

CROSS-REFERENCE TO RELATED APPLICATIONS

This is a non-provisional application being filed under 37 CFR 1.53(b) and incorporating by reference United States Provisional Application for patent that was filed on Jul. 16, 2008 and assigned Ser. No. 61/081,110, such application is attached hereto as Appendix A in its entirety.

TECHNOLOGY FIELD

The present transducer generally relates to the field of high power ultrasonic transducers and particularly to transducers for high power ultrasonic therapy.

BACKGROUND

Application of ultrasound for medical diagnostic purposes is well known. However, the development of therapeutic applications of ultrasound is a relatively new and rapidly developing technology. Treatment by ultrasound has many advantages and it is generally acknowledged that there are fewer side effects compared with other therapeutic treatment techniques.

In order to cause a desired therapeutic effect, application of ultrasound requires ultrasound power in order of more than a magnitude higher than the one required for diagnostic purposes. Ultrasound is introduced into the treated subject with the help of an ultrasound transducer. An ultrasound transducer is a device that converts electric energy into ultrasound energy or ultrasound waves. Usually, this term refers to piezoelectric transducers that convert electrical energy into ultrasound. Accordingly, advances in transducer technology play an important role in this technological area.

Specific characteristics of a high power ultrasound transducer relate to the ability of providing and sustaining without damage high peak power with high duty cycles; focusing ultrasound and focal spot location control; access to deeper layers of treated tissue, and providing a feedback to control equipment enabling the operator of changing treatment parameters.

Typical high power transducers used for therapeutic treatment are composed of piezoelectric material plates, having conducting electrodes on both sides and driven by an alternating voltage (alternating current—AC) electrical power generator. The typical operating frequency of these transducers is in the range from 100 kHz to 5 MHz. Usually, transducer side applied to the treatment location has an acoustic impedance matching element to compensate for the large difference between the transducer acoustic impedance and the treated subject acoustic impedance. The opposite side of the piezoelectric material is coupled with either ultrasound reflecting or absorbing material. Efficient use of the energy generated by high power ultrasound transducers is imperative and therefore absorbing backings are not used. The absorbing backing is usually replaced by a backing having large acoustic impedance mismatch with the piezoelectric ceramics that reflects most of the ultrasound energy, since such structure reduces ultrasound energy waste. The reflecting material can be one with acoustic impedance significantly different from that of the piezoelectric material.

Air is the best reflecting material; however, air cannot be used for high power transducers, where heat removal is a major problem. Piezoelectric ceramic must be provided with a way to remove heat efficiently and air does not possess proper thermal conductivity properties. Oil or solid material with high thermal conductivity are more frequently used for high power ultrasound transducers. The efficient heat removal requirement contradicts some of the solutions used for good ultrasound coupling.

Phased array transducers are more effective than conventional planar or curved piezoelectric transducers and they are typically used for high power ultrasound treatment applications. Phased array transducers are made by cutting the piezoelectric materials into individual piezoelectric elements—sometimes termed "pixels", with each pixel having its own-wired connection to an allocated electrical driver. By controlling the phases of each of the electrical drivers, the ultrasound beam could be electronically scanned in the treated location. The phased array structure also has the advantage of reducing parasite oscillations mode compared to a single piece transducer.

Production and use of high-power phased array transducers operating at high peak power and relatively low frequencies pose a number of problems. Piezoelectric elements or pixel size and piezoelectric ceramics material thickness are in the range of a few millimeters. They are attached to the acoustic impedance matching plate with the help of adhesives or soldering, or potting of materials one on the other. The mechanical load caused by the ultrasound vibrations is maximal at the interface of the piezoelectric ceramics with the matching plate. At high peak power, the strength of bonding is not sufficient and the bonding is damaged, so the lifetime of the transducer is short. In case of over-driving the transducer, irreversible damage can occur. Soldering provides a stronger bond than gluing and because of this, instead of the bond, the ceramic piezoelectric material fails.

Electrodes soldered or glued to the piezoelectric ceramics tend to fail at high power. In some extreme cases, when indeed high ultrasound power is applied the voltage supplying wires may be cut by shear tension. Both direct gluing or soldering of conductive wires to the contacts of the piezoelectric ceramics of flexible printed circuits might fail at high power.

These and other problems are impeding faster development of the technology and should be partially or fully resolved.

SUMMARY

The high power ultrasound transducer includes piezoelectric ceramic elements located between an electrically conductive acoustic impedance matching plate and an assembly of electric contacts configured to supply voltage to each of the piezoelectric elements. A force generated by one or more resilient conductive elements pressing the piezoelectric ceramic elements against the impedance matching plate and the assembly of electric contacts, enables an electrically conductive path required for voltage supply to the piezoelectric elements.

BRIEF LIST OF DRAWINGS

The disclosure is provided by way of non-limiting examples only, with reference to the accompanying drawings. The drawings are not necessarily to scale, emphasis instead being placed upon illustrating the principles of the method.

DETAILED DESCRIPTION OF EXEMPLARY EMBODIMENTS

Figure 1:
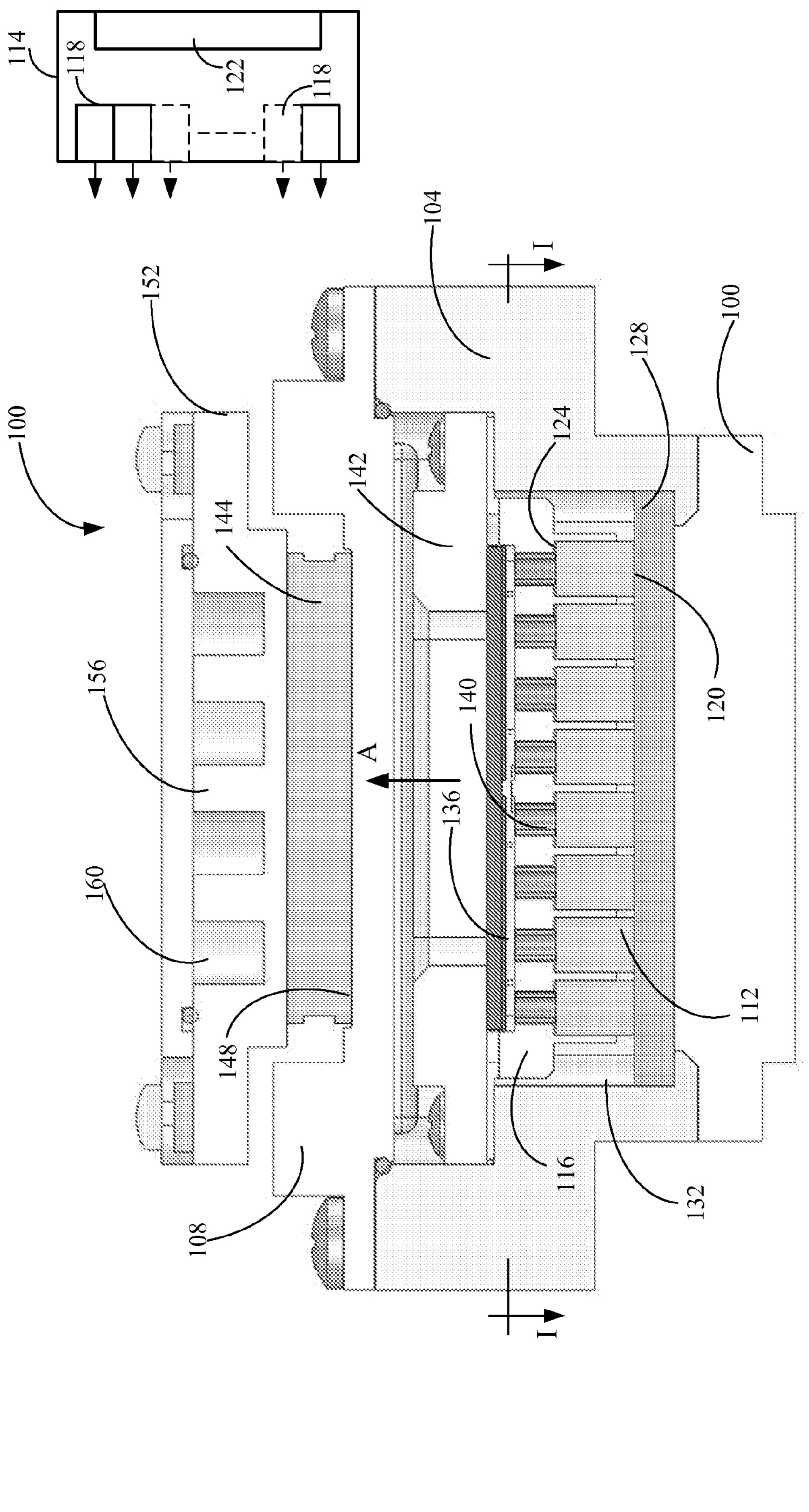
FIG. 1 is a schematic illustration of a cross section of an exemplary embodiment of the present ultrasound transducer.

The principles and execution of the high power ultrasound transducer, apparatus, and method of using the transducer described thereby may be understood by reference to the drawings, wherein like reference numerals denote like elements through the several views and the accompanying description of non-limiting, exemplary embodiments. The directional terminology, such as "up," "down," "front," "back," etc., is used with reference to the orientation of the Figure(s) being described. Because components of embodiments of the present invention can be positioned in a number of different orientations, the directional terminology is used for purposes of illustration and is in no way limiting.

Reference is made to FIG. 1, which is a schematic illustration of a cross section of an exemplary embodiment of the present ultrasound transducer. Transducer 100 comprises a housing 104 covered by a lid or cover 108. One or more piezoelectric ceramics elements 112 having contacts deposited on the lower and upper sides 120 and 124 of the piezoelectric ceramics elements 112 are arranged in a multi section bin 116, shown in more detail in FIG. 2, such that each of piezoelectric elements 112 is capable of operating independently and does not interfere with the operation of a neighboring piezoelectric element. Bin 116 with the piezoelectric elements is located in the inner cavity 132 of housing 104 such that one of the contacts of each of piezoelectric elements is in electrical communication with a conductive acoustic impedance matching material plate 128 located in the inner cavity 132 of housing 104. Impedance matching plate 128 is a mixture of conductive particles, for example metal particles or graphite powder with a resin. Epoxy may be a sample of such resin and in particular, graphite impregnated epoxy or any other conductive material impregnated polymer possessing similar properties such as epoxy. These materials are conductive and enable voltage application to contacts 120. The electrically conductive acoustic impedance matching material plate 128 represents a common electrical connection to all of the piezoelectric elements 112 of transducer 100. The matching plate can also be made of a non-conductive material, which is plated by a thin layer of conducting material such as copper or gold.

An assembly of electric contacts implemented as a rigid or flexible printed wiring board 136, metal coated ceramics, or any other form of contacts configured to provide voltage to each of piezoelectric elements 112 is connected to a source of ultrasound energy 114. Source 114 may include one or more ultrasound generators or drivers 118 operative to provide voltage to each of said piezoelectric ceramic elements 112 and a controller 122 that synchronizes operation of ultrasound generators or drivers 118 and accordingly of piezoelectric ceramic elements 112.

Resilient, electrically conductive elements 140 inserted in appropriate holes of multi section bin 116 are located between second contact 124 of piezoelectric element 112 and protruding or flat pads 130 (FIG. 4) of the assembly of electric contacts implemented as a flexible printed circuit 136. They enable an electric pass from flexible printed circuit 136 to piezoelectric ceramic elements 112. An interim plate 142 is configured to lock and slightly push circuit 136 against resilient elements 140 such that pressure applied by elements 140 is transferred to piezoelectric ceramic 112 ensuring a contact with conductive impedance matching plate 128. Cover 108 seals cavity 132. Resilient, electrically conductive elements 140 may be such as metal springs or polymeric electrically conductive materials, for example, graphite or metal particles loaded silicone or other similar polymers. The force developed by resilient elements 140 is affecting each of the piezoelectric ceramic elements 112 by pushing them against conductive impedance matching plate 128 and enabling a reliable electric contact between first end 120 of piezoelectric elements 112 and conductive acoustic impedance matching plate 128. First end of resilient elements 140 is in contact with second piezoelectric electrode 124 where the second end of resilient element 140 is in contact with pads 130 of flexible printed circuit 136.

There are no wires, conductive glue or solder applied to the piezoelectric elements and the load caused by the ultrasound vibrations at the interface of the piezoelectric ceramics 112 with the impedance matching plate 128 is not affecting the interface or the contacts.

For efficient transfer of ultrasound energy from the piezoelectric-ceramic elements 112 to the acoustic impedance matching plate 128, the space between them could be filled with fluid. Generally, if the surfaces would be ideally matched, no fluid would be required. However, in practice the surfaces are not ideally matched and efficient ultrasound coupling is easier to achieve with a coupling medium. Such medium can be a fluid, a gel or grease. Practically, most of non-solid materials with proper acoustic properties may be used as coupling material. It was found that best results are obtained with different oils, and in particular with castor oil. The oil fills the miniscule vacancies existing at the interface of the piezoelectric-ceramic 112 and the acoustic impedance matching plate 128 and forms a thin oil layer between piezoelectric elements 112 and impedance matching plate 128. The oil may fill-in cavity 132 of transducer 100 and the piezoelectric ceramic elements 112 operate being immersed in the oil. This improves heat removal from the piezoelectric elements 112 and also prevents high voltage sparking between the elements.

In addition, it was found that cooling the transducer improves the transducer performance. This characteristic can be attributed to the fact that at lower temperatures the oil viscosity increases and/or because of the reduction of the vapor pressure of the fluid. Oil, and in particular castor oil, was found to be suitable fluids to fill-in the cavity 132 of high power ultrasonic transducer 100. This is probably due to the relatively low vapor pressure of the castor oil. Fluids with high vapor pressure tend to generate cavitations bubbles under the action of high power ultrasound. The cavitations bubbles absorb energy and may cause damage to the transducer components.

Experiments showed that degassing of the oil filling in the transducer cavity 132 increases the performance of the transducer. It is believed that this is due to reduction of air trapped in the oil and the extraction of volatile components present in the oil, which reduces the risk of cavitations. Accordingly, oil degassing is performed at a pressure lower than the vapor pressure of the volatile components of the oil. Using a fluid or non-solid material reduces the load on the transducer components, and prevents irreversible damage to the transducer even when driving the transducer at very high power. Absence of solid and fixed contact between the piezoelectric ceramic elements 112 and the matching plate 128 further alleviates the possible damage to the transducer components participating in the process.

The acoustic impedance matching plate 128, made as mentioned above from epoxy-impregnated graphite, in addition to being a good electric conductor is also a good heat conductor. The heat generated in the course of operation of the piezoelectric ceramic elements 112 flows through the impedance matching plate 128 to housing 104, which is typically made of a good heat conductor such as aluminum or copper, and through housing 104 to a thermoelectric cooler 144. The oil that fills-in inner cavity 132 of housing 104 and into which the piezoelectric ceramic elements 112 are immersed, efficiently removes the heat by conduction and by convection. Natural convection homogenizes the temperature inside cavity 132 and in case of need; a forced circulation of oil inside cavity 132 may be introduced.

Thermoelectric cooler 144 located on surface 148 of cover 108 operates to cool the housing and oil and maintain the desired transducer operating temperature. A heat sink 152 with heat distribution fins 156 and cooling fluid supply channels 160 cools the hot side of thermoelectric cooler 144. The cooling fluid may be water or any other fluid suitable for the task. The transducer with the cooling scheme described above resolves the heat removal problems and enables operation of the transducer at high ultrasound energy levels and long operating times without inducing any damage to the transducer.

Although the oil, including castor oil, is an insulator, when resilient electrically conducting elements 136 press piezoelectric-ceramic 112 with their contact 120 being in electrical communication with impedance matching plate 128, the electricity passes between them despite oil presence. One contributing factor to this characteristic is that the contact surfaces are not perfect and as indicated above, have miniscule vacancies and hills in the order of a fraction of a micron. The hills on the surface of the piezoelectric-ceramic 112 are in direct contact with hills on the surface of acoustic impedance matching plate 128 and the electricity passes through these contacts. The overall combination of hills contacting acoustic impedance matching plate 128 and vacancies filled with oil has relatively low electric resistance. The other electrode 124 of piezoelectric element/s 112 is in contact with the resilient electrically conductive element 140 pushing piezoelectric-ceramic elements 112 to matching plate 128. The electrical connection enabled by the resilient electrically conductive element 140 generates a small, practically negligible acoustical load on the piezoelectric-ceramic 112, but the high power ultrasound does not damage the voltage (electrical) supply path. The electrical connection of the piezoelectric ceramics does not contain wires, soldering or other elements typically damaged by high power ultrasound.

In an alternative embodiment, the acoustic impedance matching material or plate may be coated with a layer of conductive material.

In order to use a larger amount of the power generated by a high power ultrasound transducer, it is desired to reflect the portion of ultrasound energy propagating in the direction away from the acoustic impedance matching plate 128, as it is illustrated by arrow A. Good ultrasound reflection may be achieved at the boundary of materials having large acoustic impedance mismatch. While air or vacuum have large acoustic impedance mismatch with the piezoelectric ceramic, both have poor thermal conductivity. The same oil, that fills in cavity 132 and serves as an acoustic impedance matching and transducer cooling fluid has large mismatch of acoustic impedance with the piezoelectric-ceramics. The acoustic impedance of oil is about 1.4MR, much smaller than that of the piezoelectric-ceramic, which is about 33-34MR.

Further improvement of the transducer operation is achieved by degassing the castor oil, which fills-in cavity 132. The oil degassing process, in addition to the removal of gases dissolved in oil, facilitates reduction in concentration of volatile compounds. Degassed oil and reduced concentration of volatile compounds impede formation of cavitations bubbles in the oil that absorb certain amount of ultrasound energy and might cause damage to nearby materials.

Figure 2:
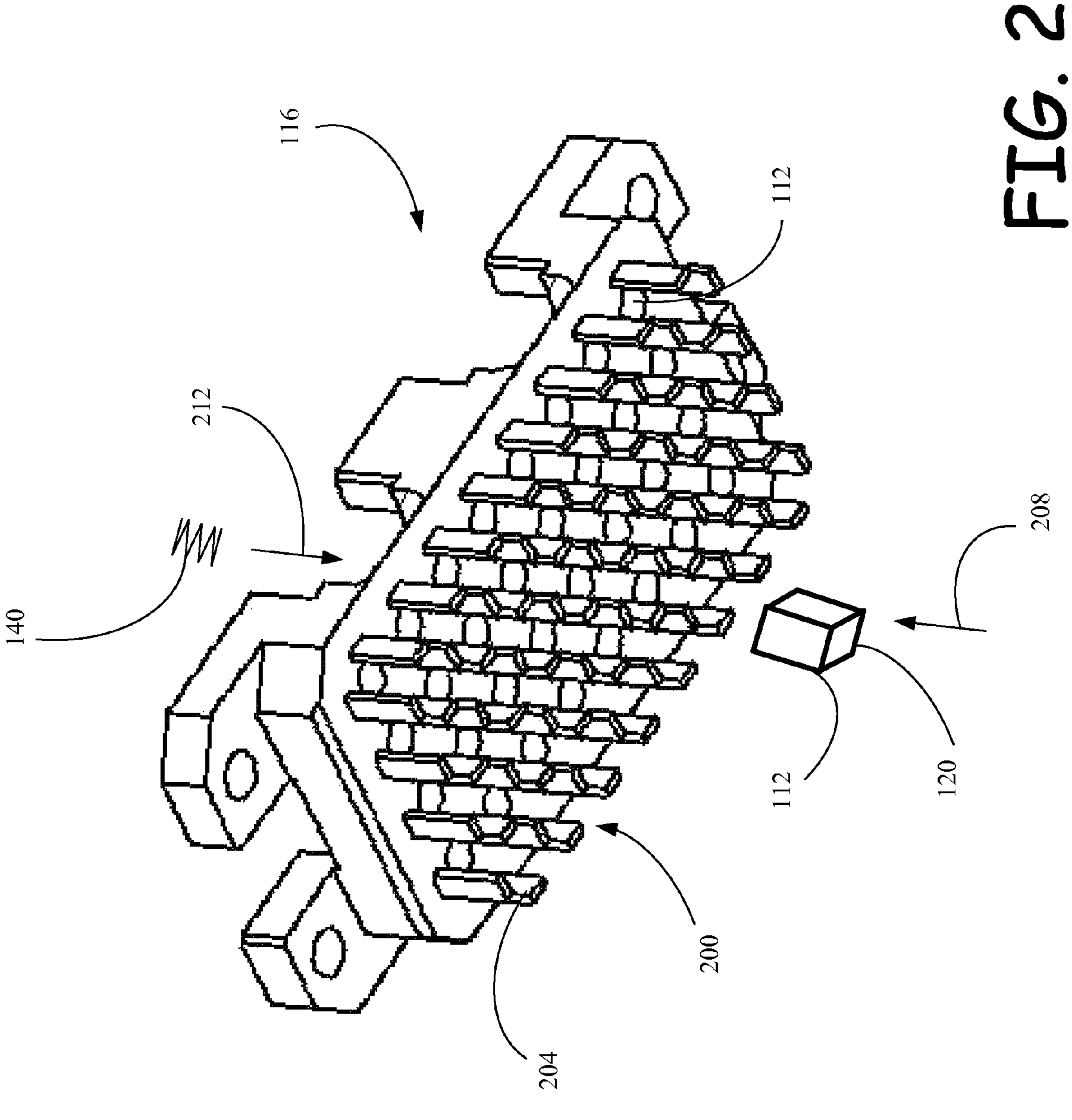
FIG. 2 is a schematic illustration of an exemplary embodiment of a multi section bin for locating and holding piezoelectric ceramic elements.

FIG. 2 is a schematic illustration of the multi-section bin 116 for locating and holding piezoelectric ceramic elements 112. Each piezoelectric element 112 is inserted into its nest 200. Walls 204 separate between the nests and piezoelectric elements 112 such that ultrasound emitted by one of the elements does not affect the neighboring elements. When bin 116 is fastened in place, it locates elements 112 such that contact 120 is enabled to be in electrical communication with acoustic impedance matching plate 128 (FIG. 1). Arrow 208 illustrates the insertion direction of piezoelectric ceramic elements 112 and arrow 212 the insertion direction of resilient conductive elements 140 shown as a spring.

Figure 3:
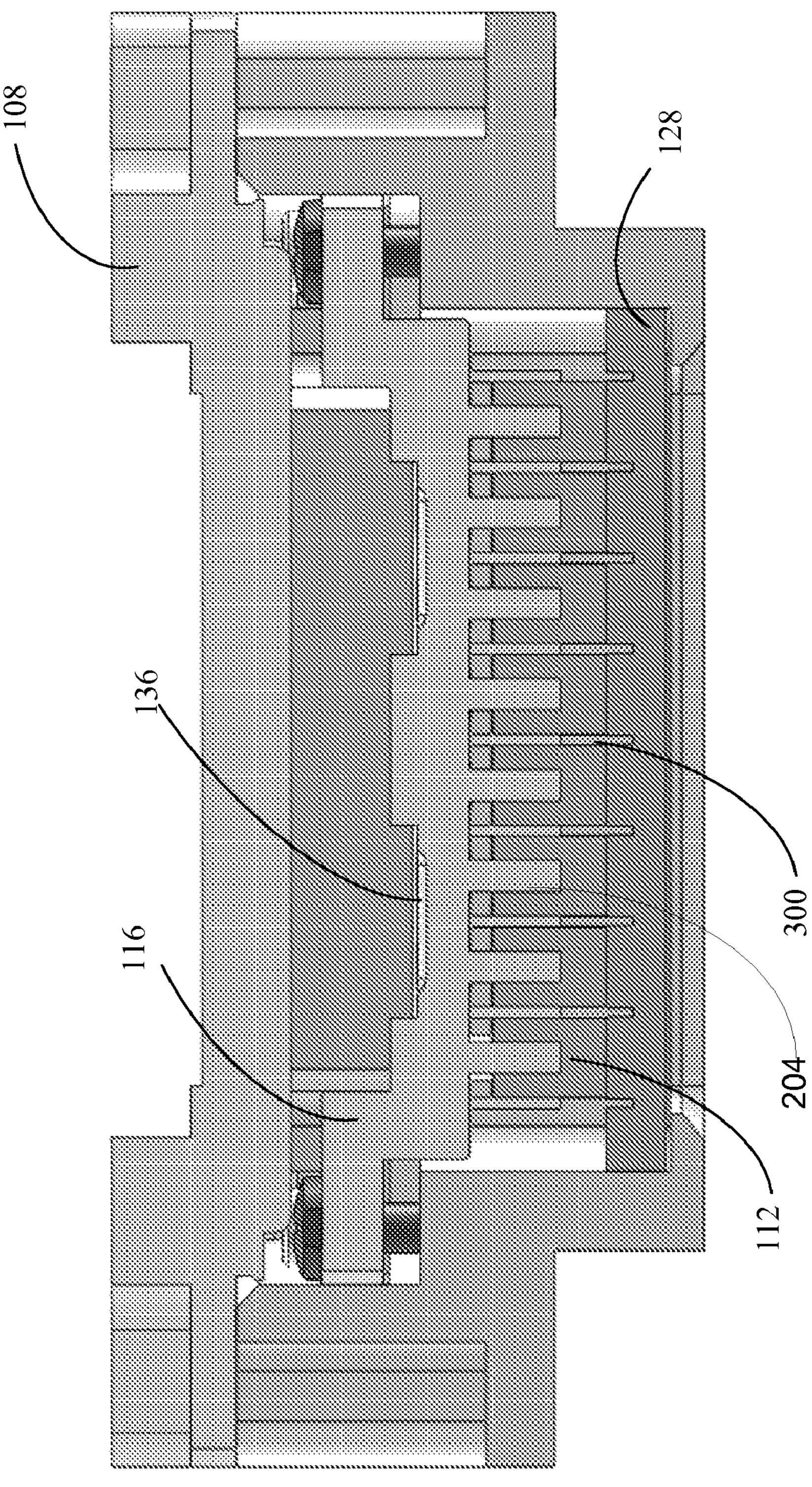
FIG. 3 is a schematic illustration of another cross section of an exemplary embodiment of the present ultrasound transducer.

FIG. 3 is a schematic illustration of an additional cross section of the present ultrasound transducer. It illustrates the location of piezoelectric ceramic elements 112, multi-section bin 116, walls 204 defining the nest 200 for each piezoelectric ceramic element 112 and flexible printed circuit 136. In one embodiment shown in FIG. 1 impedance matching plate 128 is a solid plate. In an alternative embodiment shown in FIG. 3, impedance matching plate 128 is a solid plate having on the side contacting piezoelectric ceramic elements 112 incisions 300. Incisions 300 serve to reduce acoustical coupling between the elements and surface wave propagation on the matching plate. In this way efficiency, focusing and scanning capabilities of the transducer are improved.

Figure 4:
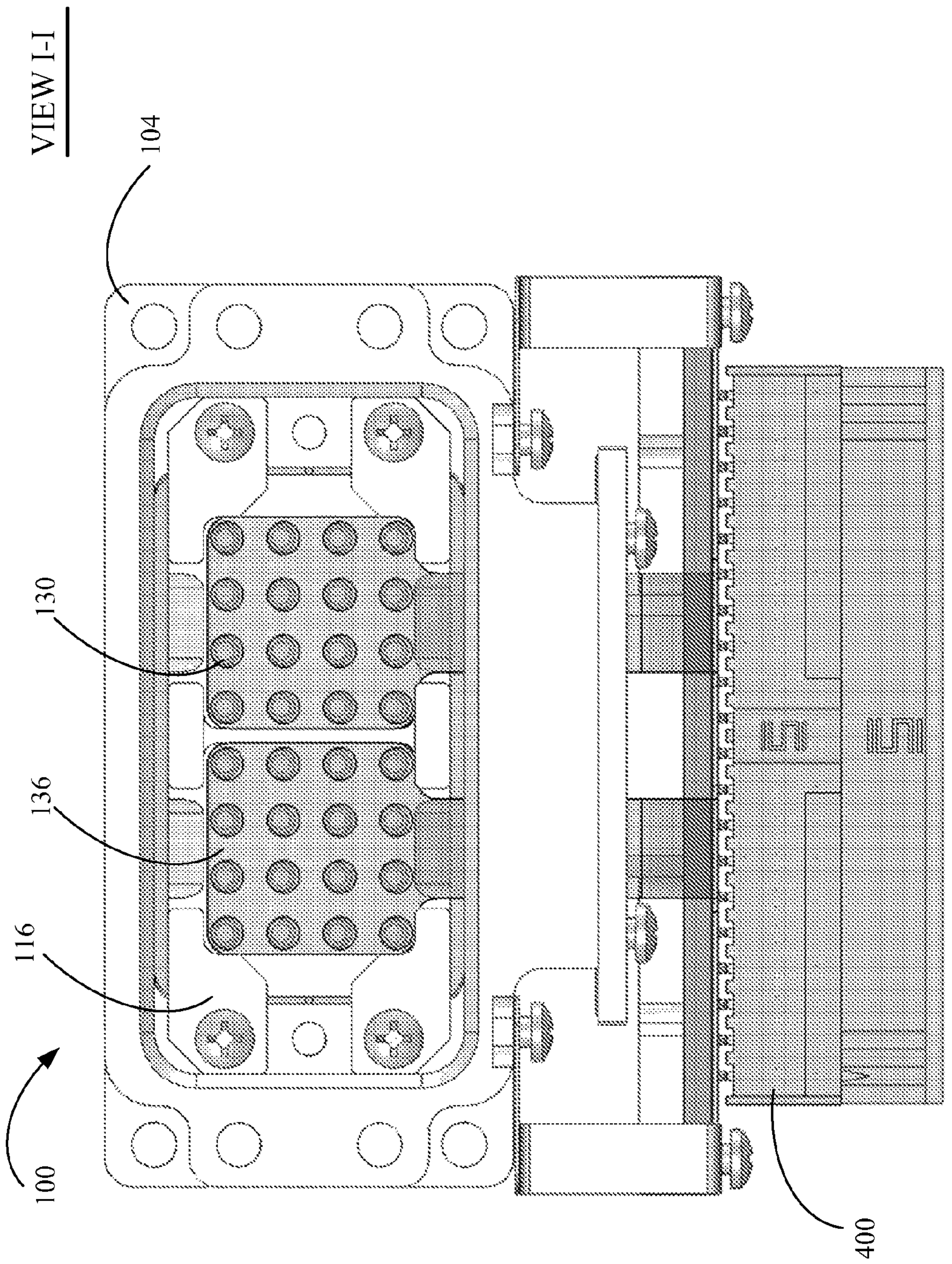
FIG. 4 is a schematic illustration of a top view of the present ultrasound transducer.

FIG. 4 is a schematic illustration of a top view of the present ultrasound transducer. Transducer 100 is shown without cover 108, thermoelectric cooler 144 and other components associated with them. Flexible printed circuit 136 contains pads 130, that may protrude over the surface of circuit 136 enabling easier contact with resilient electrically conducting elements 140. Connector 400 provides electrical connection between each of piezoelectric ceramic elements 112 and their respective drivers 118 (FIG. 1).

Figure 5A:
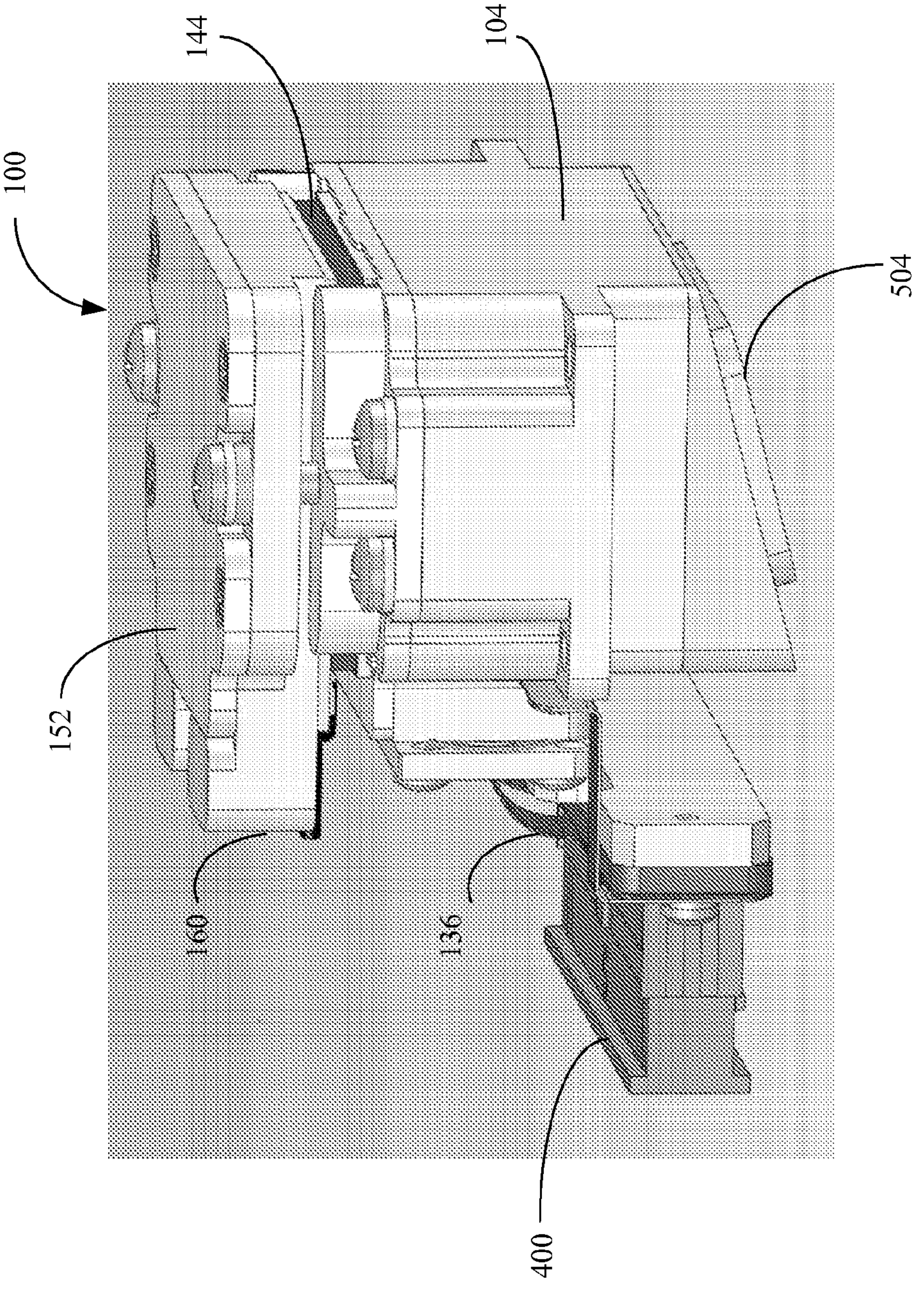
FIGS. 5A and 5B are schematic illustrations of two exemplary assemblies of the present ultrasound transducer.
Figure 5B:
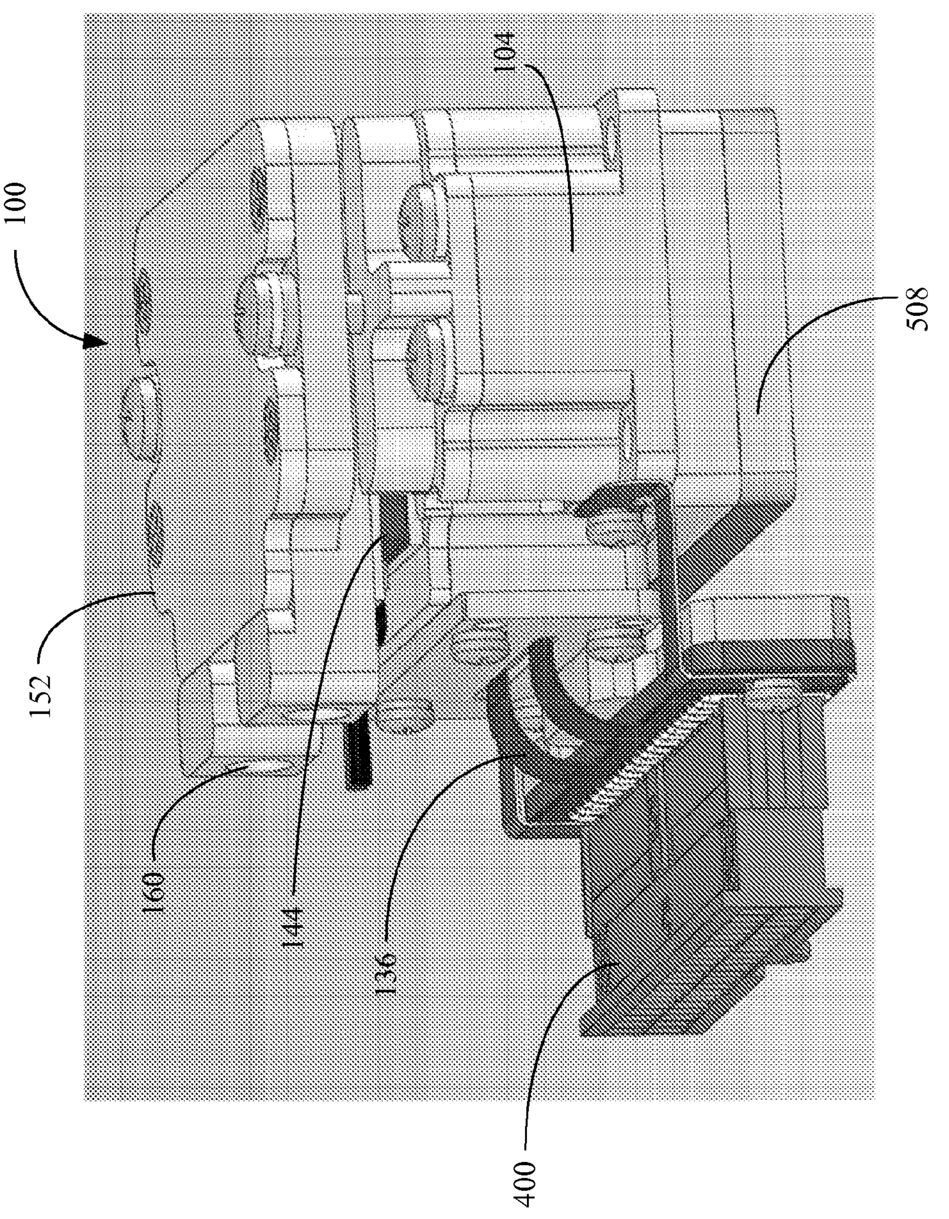

FIGS. 5A and 5B are schematic illustrations of two exemplary assemblies of the present ultrasound transducer for therapeutic use. The therapies include adipose tissue reduction, skin wrinkles elimination and some other cosmetic and therapeutic applications. Transducer 100 may be applied to tissue as a component of an ultrasound tissue treatment applicator, such as the one disclosed in U.S. provisional patent application No. 61/081,110 assigned to the same assignee and attached herein for reference purposes only as Appendix A. The transducer surface as shown in FIG. 5A that would be in contact with the tissue may be slanted to match the desired tissue protrusion angle. In order to improve ultrasound to tissue coupling, a wedge 504 is located between the tissue and the impedance matching plate 128. The wedge is made from a material having acoustic impedance close to that of the human body to prevent ultrasound reflection. Polyurethane or other suitable polymers may be used. In another embodiment illustrated in FIG. 5B, transducer 100 is adapted to contact a relatively flat portion of the tissue. In order to improve ultrasound to tissue coupling, a flat plate 508 made from polyurethane or similar is located between the tissue and the impedance matching plate 128.

The high power ultrasound transducer described above may be used in a variety of therapeutic medical application. The use of the transducer is not limited however, to medical applications only. It may be applied to different fluids mixing processes, different ultrasound cleaning applications, defect detection applications, and other applications that are in need of high ultrasound power.

Given below are typical transducer operating parameters and components that are provided by way of non-limiting examples.

The piezoelectric material for the high power transducer would typically be one of the PZT ceramics families. The oscillation frequency of the transducer is between 100 kHz to 5 MHz, or 100 kHz to 1 MHz, or 100 kHz to 400 kHz. The peak power at the transducer radiating surface may be between 10 $W/cm^2$ to 500 $W/cm^2$, or 50 $W/cm^2$ to 200 $W/cm^2$, and typical drive pulse length would be between 20 microseconds to 1 millisecond. Average ultrasound power may be between 0.1 $W/cm^2$ to 10 $W/cm^2$, or 1 $W/cm^2$ to 3 $W/cm^2$. Typical number of piezoelectric ceramic elements in a transducer may be between 4 to 128, or 8 to 64, with the size of each of the elements (pixels) in the array ranging from 1×1×1 mm and up to 6×6×10 mm.

A number of embodiments have been described. Nevertheless, it will be understood that various modifications may be made without departing from the spirit and scope of the ultrasound transducer. Accordingly, other embodiments are within the scope of the following claims.

What is claimed is:

1. A high power ultrasound transducer, said transducer comprising: a plurality of piezoelectric elements, a conductive acoustic impedance matching plate, and an assembly of electric contacts arranged to provide voltage to each of said piezoelectric elements;

a plurality of resilient electrically conductive elements generating a force and pressing said piezoelectric ceramic elements against said matching plate and enabling an electrically conductive path that is free of glue, solder and wire between said piezoelectric elements and said impedance matching plate, and between said piezoelectric elements and said assembly of electric contacts; and a thin non-solid material layer disposed between the piezoelectric ceramic elements and the acoustic impedance matching plate.

2. The high power ultrasound transducer according to claim 1, wherein the impedance matching plate is made of a mixture of electrically conductive particles with a resin.

3. The high power ultrasound transducer according to claim 2, wherein the electrically conductive particles are at least one of a group of metal particles and graphite powder.

4. The high power ultrasound transducer according to claim 2, wherein the resin is epoxy.

5. The high power ultrasound transducer according to claim 1, wherein the impedance matching plate is electrically conductive.

6. The high power ultrasound transducer according to claim 1, wherein the impedance matching plate is thermally conductive.

7. The high power ultrasound transducer according to claim 1, wherein the impedance matching plate is plated with a thin layer of electrically conductive material.

8. The high power ultrasound transducer according to claim 1, wherein the assembly of electric contacts is at least one of a group of rigid printed wiring boards, flexible printed wiring boards, and metal coated ceramics.

9. The high power ultrasound transducer according to claim 1, wherein the resilient electrically conductive elements are at least one of a group of metal springs and polymeric electrically conductive materials.

10. The high power ultrasound transducer according to claim 1, wherein the thin non-solid material layer is one of a group of oil, acoustic impedance matching gel, and a non-solid material.

11. The high power ultrasound transducer according to claim 10, wherein the thin non-solid material layer is castor oil.

12. The high power ultrasound transducer according to claim 1, wherein the thin non-solid material layer is castor oil.

13. The high power ultrasound transducer according to claim 1, wherein the piezoelectric ceramics elements are immersed in oil.

14. The high power ultrasound transducer according to claim 13, wherein the oil is a castor oil.

15. The high power ultrasound transducer according to claim 10, wherein the oil is a degassed to reduce air and concentration of volatile compounds.

16. The high power ultrasound transducer according to claim 10, wherein said oil reflects the ultrasound energy generated by the piezoelectric ceramic elements.

17. The high power ultrasound transducer according to claim 10, wherein the oil homogenizes temperature of the transducer.

18. The high power ultrasound transducer according to claim 1, further comprising a housing made of a heat conducting material.

19. The high power ultrasound transducer according to claim 1, further comprising a thermoelectric cooler operative to maintain transducer temperature within a desired range.

20. An apparatus for ultrasound tissue treatment, said apparatus comprising:

a plurality of ultrasound generators; and an ultrasound transducer with one or more piezoelectric ceramics elements, a conductive acoustic impedance matching plate, resilient electrically conductive elements, an assembly of electric contacts enabling a non-glued, non-soldered and non-wired electric contact between the piezoelectric ceramic elements, impedance matching plate, and voltage supplying elements of said transducer, and a thin non-solid material layer disposed between the piezoelectric ceramic elements and the acoustic impedance matching plate.

21. The apparatus for ultrasound tissue treatment according to claim 20, wherein the ultrasound transducer further comprises an electrically conductive acoustic impedance matching plate serving as a common electrode to the piezoelectric ceramic elements and a temperature homogenizing fluid.

22. The apparatus for ultrasound tissue treatment according to claim 21, wherein the voltage supplying elements of the transducer are the acoustic impedance matching plate and the assembly of electric contacts.

23. The apparatus for ultrasound tissue treatment according to claim 20, wherein the voltage supplying elements of the transducer are the acoustic impedance matching plate and the assembly of electric contacts.

24. The apparatus for ultrasound tissue treatment according to claim 20, wherein the thin non-solid material layer is one of a group of oil and acoustic impedance matching gel.

25. The apparatus for ultrasound tissue treatment according to claim 20, wherein the thin non-solid material layer is castor oil.

26. A method for providing an electric contact in a high power ultrasound transducer, said method comprising:

providing a plurality of piezoelectric ceramic elements, a conductive acoustic impedance matching plate and an assembly of electric contacts configured to supply voltage to each of said piezoelectric ceramics elements;

positioning resilient conductive elements between said piezoelectric ceramic elements and said assembly, pressing the piezoelectric elements against the impedance matching plate and ensuring a free of glue, solder, and wire electrical contact with said matching plate and the assembly of electric contacts; and providing a thin non-solid material layer disposed between the piezoelectric ceramic elements and the acoustic impedance matching plate.

27. The method according to claim 26, wherein also filling the gaps between the piezoelectric ceramic elements and the acoustic impedance matching plate with said non-solid material.

28. A high power phased array ultrasound transducer, said transducer comprising:

a plurality piezoelectric ceramic elements;

an electrically conductive acoustic impedance matching plate;

an assembly of electric contacts configured to supply voltage to each of said piezoelectric elements;

one or more resilient conductive elements located between said piezoelectric elements and the assembly of electric contacts pressing the piezoelectric elements against the impedance matching plate and enabling a non-glued, non-soldered and non-wired electrically conductive path between said piezoelectric elements and said plate and between said piezoelectric elements and said assembly of electric contacts; and a thin non-solid material layer disposed between the piezoelectric ceramic elements and the acoustic impedance matching plate.

29. The high power phased array ultrasound transducer according to claim 28, wherein said pressing of the piezoelectric ceramics enables electric contact with said impedance matching plate.

30. The high power phased array ultrasound transducer according to claim 28, wherein said impedance matching plate is a common electrode to said one or more of piezoelectric ceramics elements.

31. An apparatus for ultrasound tissue treatment, said apparatus comprising:

a plurality of ultrasound generators;

an electrically conductive acoustic impedance matching plate;

an ultrasound transducer with one or more piezoelectric ceramics elements, resilient electrically conductive elements, and voltage supplying elements enabling electrical contact between the piezoelectric ceramic elements and the voltage supplying elements of said transducer;

resilient electrically conductive elements pressing the piezoelectric ceramics elements against the electrically conductive acoustic impedance matching plate and enabling a non-glued, non-soldered and non-wired electrically conductive path between said piezoelectric ceramics elements and said electrically conductive acoustic impedance matching plate;

a controller operative to control said ultrasound generators, provide voltage to each of said piezoelectric ceramics element and synchronize their operation; and a thin non-solid material layer disposed between the piezoelectric ceramic elements and the acoustic impedance matching plate.

32. The apparatus for ultrasound tissue treatment according to claim 19, further comprising a controller operative to control said ultrasound generators, provide voltage to each of said piezoelectric ceramics element and synchronize their operation.

33. A high power phased array ultrasound transducer, said transducer comprising:

an electrically conductive acoustic impedance matching plate; one or more piezoelectric ceramic elements having an electrical contact on a first side with said plate and on a second side with one or more resilient conductive elements located between said piezoelectric elements and an assembly of electric contacts configured to supply voltage to each of said piezoelectric elements;

an interim plate configured to lock and push said assembly of electric contacts against said resilient elements such that pressure applied by said resilient elements is transferred to said piezoelectric elements ensuring a non-glued, non-soldered and non-wired contact with said matching plate; and a thin non-solid material layer disposed between the piezoelectric ceramic elements and the acoustic impedance matching plate.

34. The high power ultrasound transducer according to any one of claims 1 and 28, wherein also comprising an interim plate configured to lock and push said assembly of electric contacts against said resilient elements such that pressure applied by said resilient elements is transferred to said piezoelectric elements ensuring contact with said matching plate.

35. The method according to claim 26, wherein also comprising locking and pushing said assembly of electric contacts against said resilient elements such that pressure applied by said resilient elements is transferred to said piezoelectric elements ensuring contact with said matching plate.

* * * * *